(12) United States Patent
Georgian

(10) Patent No.: US 11,490,800 B2
(45) Date of Patent: Nov. 8, 2022

(54) LAPAROSCOPIC EYE WIPER

(71) Applicant: Stelian Valeriu Georgian, Altamonte Springs, FL (US)

(72) Inventor: Stelian Valeriu Georgian, Altamonte Springs, FL (US)

(*) Notice: Subject to any disclaimer, the term of this patent is extended or adjusted under 35 U.S.C. 154(b) by 0 days.

(21) Appl. No.: 15/180,782

(22) Filed: Jun. 13, 2016

(65) Prior Publication Data
US 2016/0360955 A1    Dec. 15, 2016

Related U.S. Application Data

(60) Provisional application No. 62/174,177, filed on Jun. 11, 2015.

(51) Int. Cl.
| | | |
|---|---|---|
| *A61B 1/12* | (2006.01) | |
| *A61B 1/313* | (2006.01) | |
| *G02B 27/00* | (2006.01) | |
| *A61B 90/70* | (2016.01) | |

(52) U.S. Cl.
CPC ............ *A61B 1/126* (2013.01); *A61B 1/3132* (2013.01); *A61B 90/70* (2016.02); *G02B 27/0006* (2013.01); *A61B 2090/701* (2016.02)

(58) Field of Classification Search
CPC ..... A61B 1/126; A61B 1/121; A61B 1/00066; A61B 1/122
USPC .................................................. 600/133, 131
See application file for complete search history.

(56) References Cited

U.S. PATENT DOCUMENTS

| | | | | |
|---|---|---|---|---|
| 1,818,670 | A * | 8/1931 | Bixler | A61M 5/24 604/234 |
| 5,188,630 | A * | 2/1993 | Christoudias | A61B 17/00234 604/1 |
| 5,203,767 | A * | 4/1993 | Cloyd | A61F 13/36 604/11 |
| 5,295,952 | A * | 3/1994 | Pietrafitta | A61B 10/04 604/1 |
| 5,337,730 | A * | 8/1994 | Maguire | A61B 1/00091 600/157 |
| 5,392,766 | A * | 2/1995 | Masterson | A61B 1/0008 15/244.1 |
| 5,413,580 | A * | 5/1995 | Stephenson | A61B 17/320036 30/315 |
| 5,514,084 | A * | 5/1996 | Fisher | A61B 1/126 600/157 |
| 5,518,502 | A * | 5/1996 | Kaplan | A61B 1/126 600/156 |
| 5,630,795 | A * | 5/1997 | Kuramoto | A61B 1/00068 600/153 |
| 5,910,105 | A * | 6/1999 | Swain | A61B 1/00128 600/104 |
| 6,312,394 | B1 * | 11/2001 | Fleming, III | A61B 10/025 600/567 |
| 6,695,772 | B1 * | 2/2004 | Bon | A61B 17/3421 600/114 |

(Continued)

*Primary Examiner* — Matthew J Kasztejna
(74) *Attorney, Agent, or Firm* — Furr Law Firm; Jeffrey M. Furr, Esq.

(57) ABSTRACT

The present invention is a Laparoscopic Eye Cleaner that can be used intra-abdominally. This laparoscopic instrument will save time and money. The instrument is a handle connected to a flat, thin stem and made of plastic or stainless steel with a soft absorbable tip. It only takes two fingers to use it. The tip that cleans the eye of the lens without the need for the laparoscope having to be removed.

7 Claims, 5 Drawing Sheets

(56) References Cited

U.S. PATENT DOCUMENTS

| | | | |
|---|---|---|---|
| 6,755,782 B2* | 6/2004 | Ogawa | A61B 1/00087 600/127 |
| 6,923,759 B2* | 8/2005 | Kasahara | A61B 1/00087 600/121 |
| 7,316,683 B2* | 1/2008 | Kasahara | A61B 17/3421 606/45 |
| 7,534,250 B2* | 5/2009 | Schaeffer | A61M 16/0472 606/191 |
| 7,918,783 B2* | 4/2011 | Maseda | A61B 1/018 600/104 |
| 7,959,561 B2* | 6/2011 | Akui | A61B 1/00087 600/121 |
| 8,105,231 B2* | 1/2012 | Kasahara | A61B 17/3421 600/104 |
| 8,267,896 B2* | 9/2012 | Hartoumbekis | A61B 1/126 604/167.01 |
| 8,668,642 B2* | 3/2014 | Kleyman | A61B 17/3423 600/204 |
| 8,690,764 B2* | 4/2014 | Clark | A61B 1/00091 600/156 |
| 8,752,230 B2* | 6/2014 | Brand | B25G 1/00 15/104.16 |
| 8,764,783 B2* | 7/2014 | Ihde, II | A61B 17/3421 15/210.1 |
| 9,232,935 B2* | 1/2016 | Brand | A61B 1/00131 |
| 9,486,129 B2* | 11/2016 | Rodriguez Sanjuan | A61B 1/122 |
| 9,763,567 B2* | 9/2017 | O'Prey | A61B 1/126 |
| 2002/0022762 A1* | 2/2002 | Beane | A61B 1/122 600/101 |
| 2002/0065450 A1* | 5/2002 | Ogawa | A61B 1/00087 600/157 |
| 2003/0139649 A1* | 7/2003 | Kasahara | A61B 1/00087 600/157 |
| 2008/0234696 A1* | 9/2008 | Taylor | A61B 17/00234 606/114 |
| 2009/0105543 A1* | 4/2009 | Miller | A61B 1/122 600/155 |
| 2009/0264703 A1* | 10/2009 | Pribanic | A61B 1/0008 600/121 |
| 2013/0031735 A1* | 2/2013 | Brand | B25G 1/00 15/104.93 |
| 2013/0305469 A1* | 11/2013 | Rodriguez Sanjuan | A61B 1/122 15/104.05 |
| 2016/0249896 A1* | 9/2016 | Bippart | A61B 17/0057 606/213 |
| 2018/0344141 A1* | 12/2018 | Rosenbaum | A61B 17/3415 |
| 2020/0060536 A1* | 2/2020 | Rylander | A61B 1/00135 |

* cited by examiner

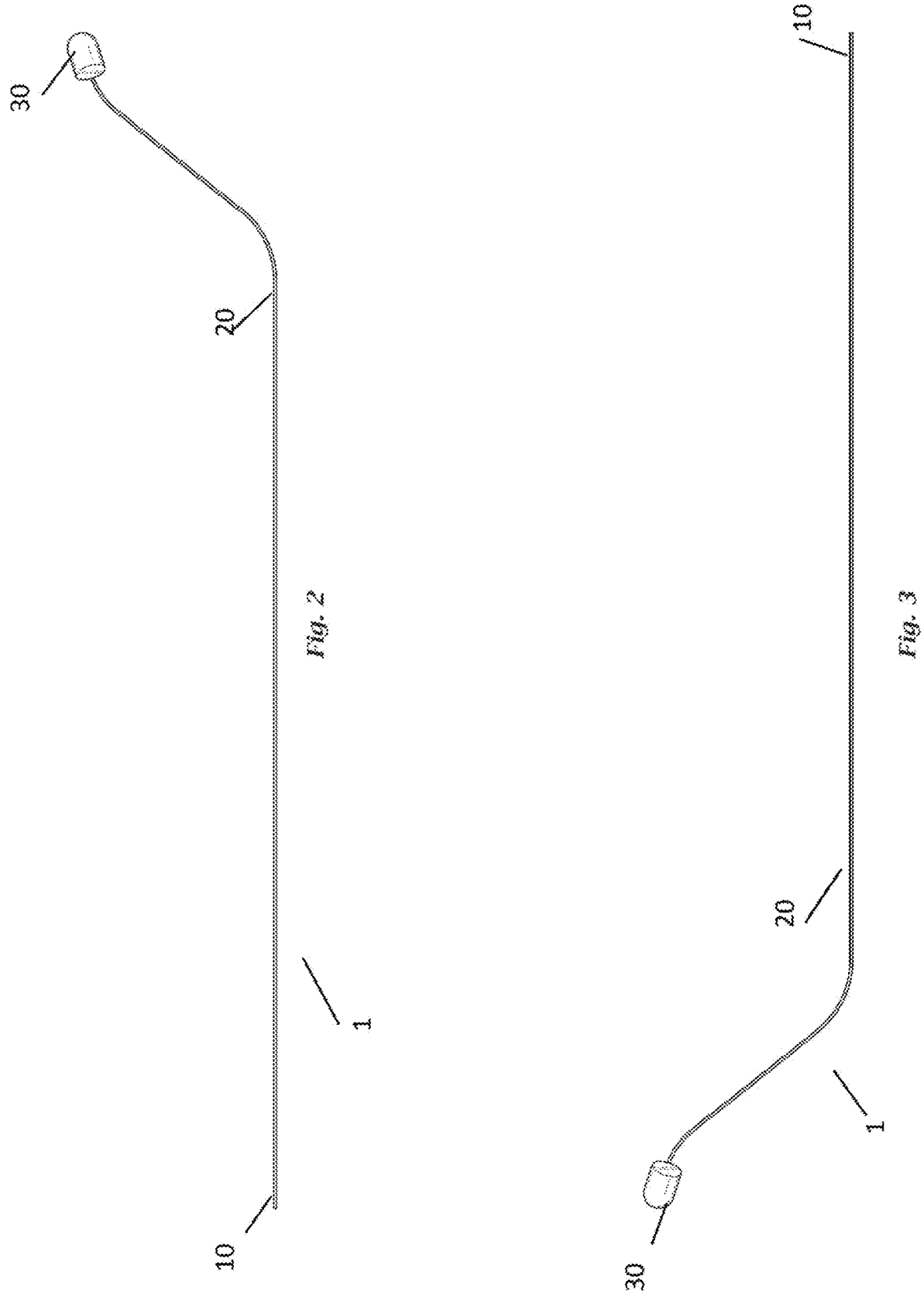

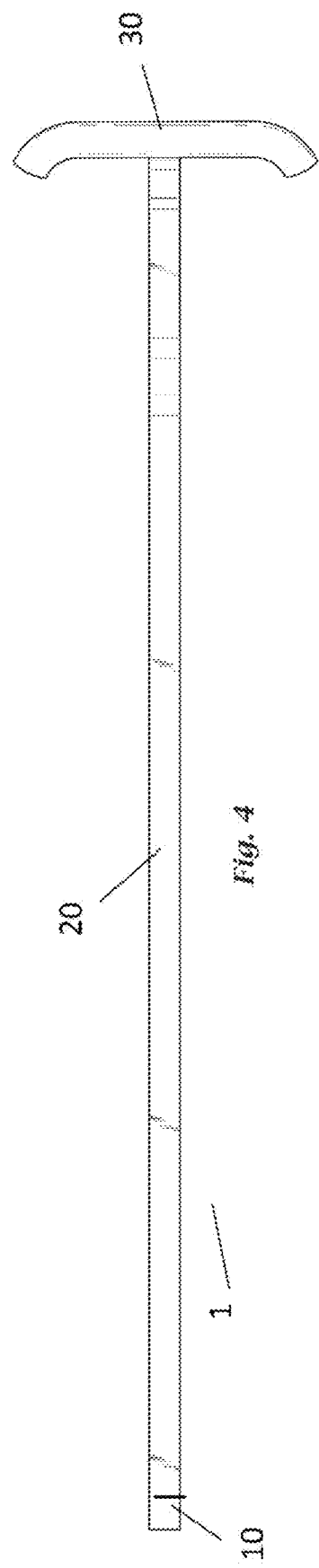
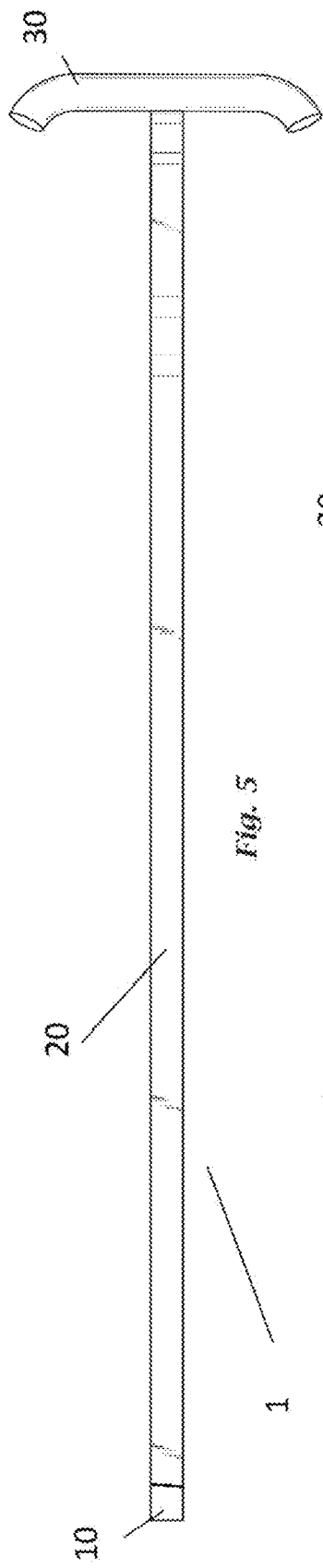
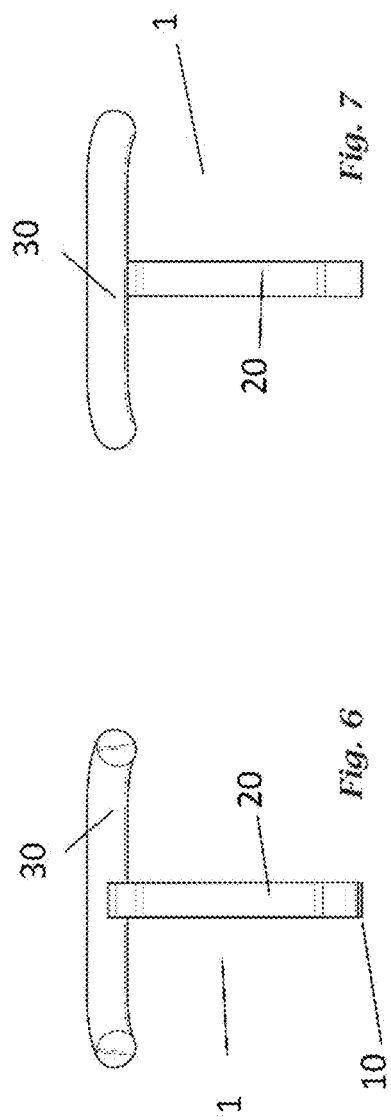

LAPAROSCOPIC EYE WIPER

CROSS-REFERENCES TO RELATED APPLICATIONS (IF ANY)

This application claims the priority date of Provisional Application No. 62/174,177 filed on Jun. 11, 2015.

BACKGROUND

1. Field of the Invention

The present invention relates to a Laparoscopic Eye Cleaner device and more particular one that cleans intra-abdominally.

2. Description of Prior Art

Laparoscopic surgery has overtaken many abdominal and thoracic procedures. Between cholecystectomy, appendectomy, hernia repair, bowel resection and a range of other therapeutic and diagnostic (i.e., exploratory surgery) procedures, there are upwards of 7.5 million laparoscopic procedures performed annually worldwide. Growth in laparoscopic surgery, which has been aggressive since the advent of laparoscopic surgery in the early 1990s, has begun to slow as many physicians have integrated lap surgery into all applicable procedures and, in some cases, over-extended its utility in more complex, higher risk procedures resulting in avoidable complications. Moreover, procedure approaches such as natural orifice transluminal endoscopic surgery, which further reduce the invasiveness of common endoscopic procedures are posing a challenge to laparoscopic procedures.

As a surgical technologist since 1998, laparoscopic and robotic procedures seems to be advancing in our society. Laparoscopic means that the doctors just create 3-5 holes the size of a quarter, instead of large incision cutting through layers of tissue. During these procedures, the eye of the scope will ALWAYS need to be cleaned intraoperative. There is a lot of time waste cleaning: bad for the patient under anesthesia!!

The general way in which laparoscopes are cleaned during surgery is to remove the scope from the patient and to clean the lens manually. There are a variety of products that promise to clean the lens faster and more efficiently when the scope is removed, but as for products that clean the lens without removing the scope, there are very few options.

The cleaning the scope in today's scenario with the need to remove increases the chances of infection. There is still room for improvement in the art.

SUMMARY OF THE INVENTION

The current invention involves a Laparoscopic Eye Cleaner that can be used intra-abdominally.

The Laparoscopic Eye Cleaner is an instrument that has a handle connected to a flat, thin stem with a soft absorbable tip. It is designed with two finger grips so that it only takes two fingers to use it. The tip that cleans the eye of the lens without the need for the laparoscope having to be removed.

The Laparoscopic Eye Cleaner can be made out of stainless steel or can be made out of plastic which could be disposable after use.

The Laparoscopic Eye Cleaner is more efficient, effective, accurate and functional than the current art.

BRIEF DESCRIPTION OF THE DRAWINGS

Without restricting the full scope of this invention, the preferred form of this invention is illustrated in the following drawings:

FIG. 2 is a right elevation of the Laparoscopic Eye Wiper;

FIG. 3 is a left elevation view of the Laparoscopic Eye Wiper;

FIG. 4 is a top plan view of the Laparoscopic Eye Wiper;

FIG. 5 is a bottom plan view of the Laparoscopic Eye Wiper;

FIG. 6 is a front elevation view of the Laparoscopic Eye Wiper;

FIG. 7 is a rear elevation view of the Laparoscopic Eye Wiper;

DESCRIPTION OF THE PREFERRED EMBODIMENT

There are a number of significant design features and improvements incorporated within the invention.

The present invention, as shown in FIGS. 1-7, is a Laparoscopic Eye Cleaner 1 that can be used intra-abdominally.

Figure 8:
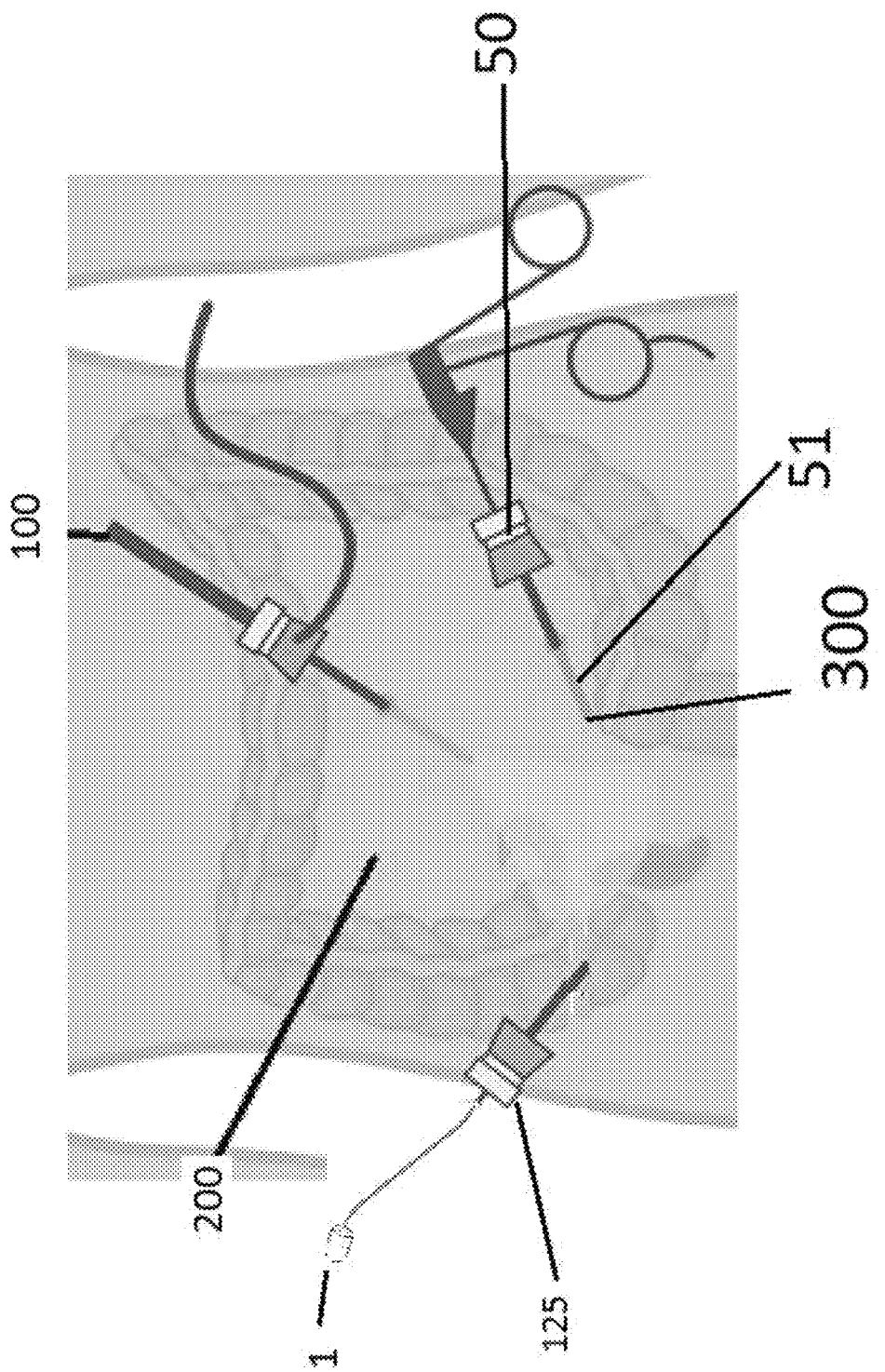
FIG. 8 shows the wiper in use.

The Laparoscopic Eye Cleaner 1 is an instrument that is s flat, thin stem and made of plastic or stainless steel with a soft absorbable tip 10. The tip 10 that cleans the eye of the laparoscope lens without the need for the laparoscope having to be removed, see FIG. 8.

Figure 1:
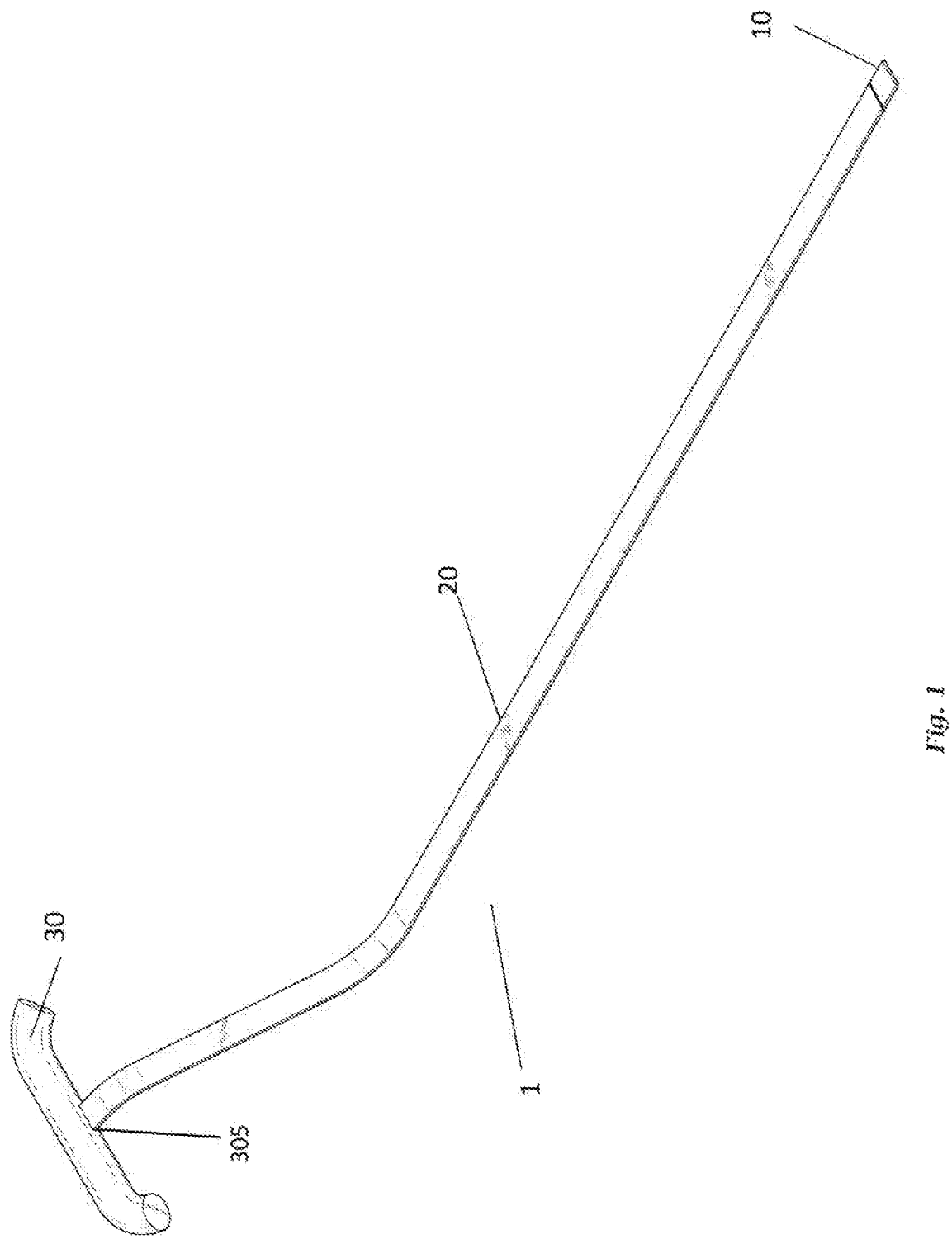
FIG. 1 is a perspective view of the Laparoscopic Eye Wiper.

The Laparoscopic Eye Cleaner 1 consists of a handle 30 connect to a a flat, thin stem 20 with a soft absorbable tip 10 as shown in FIG. 1. The Laparoscopic Eye Cleaner 1 is in a "T" shape.

The handle 30 is designed with two finger grips so that it only takes two fingers to use it. It extends perpendicular from the stem 20. In the preferred embodiment, the handle 30 is made of a circular rod with the ends bending slightly inward towards the stem 20. This design is to make it easy to hold and control with two fingers.

The stem 20 is flat and thin. It has a slight downward slope from its attachment point to the handle 30 and then curves slightly up so that the distal end is aligned with the proximal end attached to the handle 30.

The tip 10 is at the end of the stem 20 opposite the stem's 20 connection to the handle 30. The tip 10 will be made of a soft absorbable material. It is the tip 10 the cleans the lens of the laparoscope.

The Laparoscopic Eye Cleaner 1 can be made out of stainless steel or can be made out of plastic which could be disposable after use.

Figure 9:
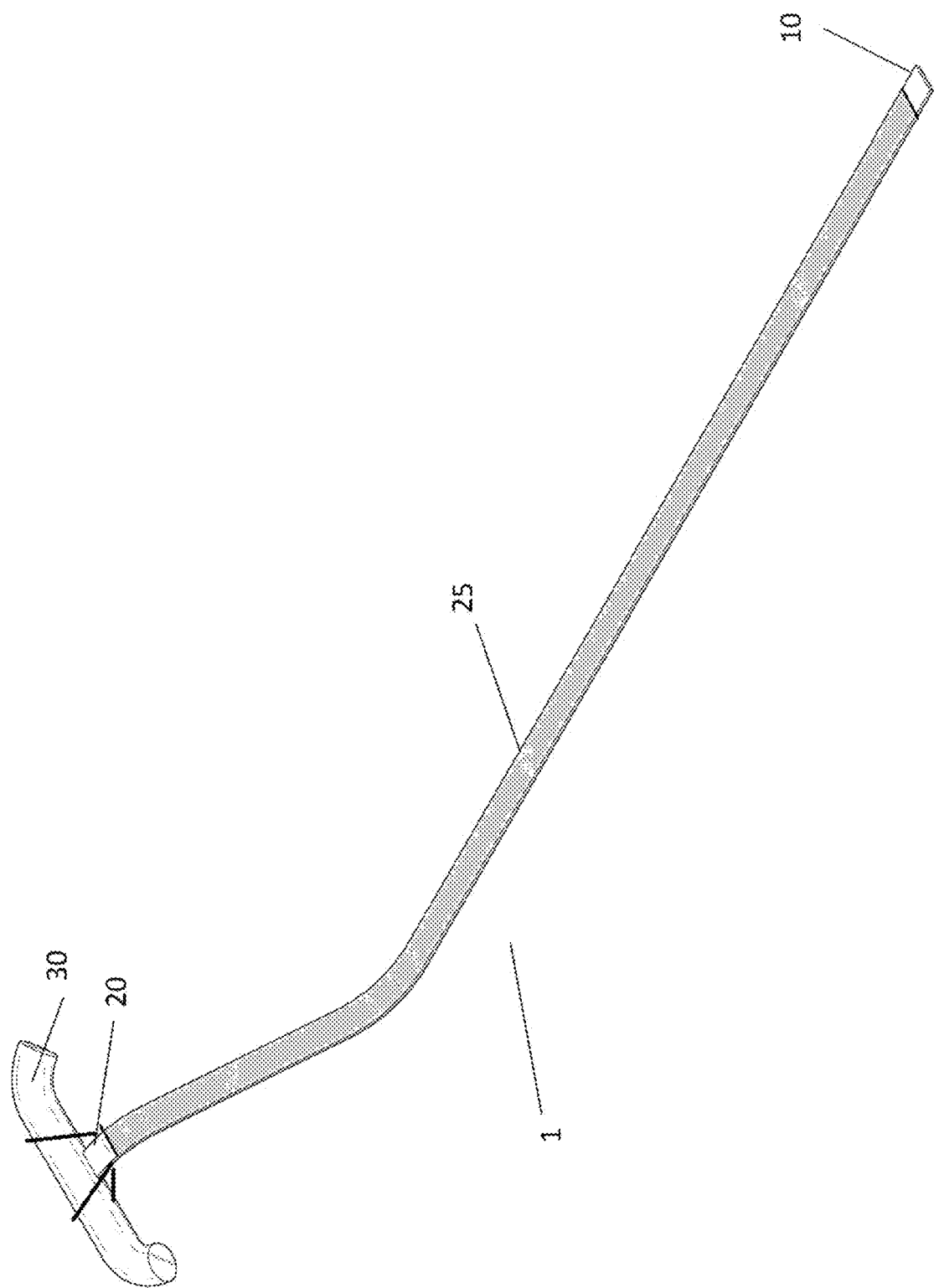
FIG. 9 shows the wiper with a sleeve.

Taking in consideration cost effectiveness for the health care facilities, when the Laparoscopic Eye Cleaner instrument 1 is made of stainless steel it may come with a fabric sleeve 25 as shown in FIG. 9. The sleeve 25 would be put over the stem 20 and attached at the handle 30, so it isn't lost in the abdomen. The sleeve 25 would be a one-time use and then discarded; the Wiper body would be reprocessed with the rest of the instruments. The tip 10, in this embodiment, would be part of the sleeve 25.

For cost effectiveness, the plastic Wiper 1 can be disposable also. There is no sleeve with the disposable Wiper, because the tip 10 would be manufactured softer.

Operation

The Laparoscopic Eye Cleaner works very simply and effectively and fast. The Laparoscopic Eye Cleaner 1 is inserted in any sleeve 125 into the body cavity. When the user watches the monitor, they bring the Laparoscopic Eye Cleaner 1 towards the eye 51 of the Laparoscope 50 and wipe as shown an appendectomy in FIG. 8. The cleaning is done intra-abdominally 100 within the body 200 of the patient.

Advantages

The advantages are; cleaning the scope within 5 seconds, maintaining the integrity of the sterile field, by not moving camera and light cords around, not taking scope out of the abdomen any more meaning the surgery does not have to stop, no distractions for the surgeon, no fogging of lens, no re-cleaning over and over and over again of the lens upon reentering the sleeve due to debris caught in the rubber seal itself initially when the scope was first pulled out.

Although the present invention has been described in considerable detail with reference to certain preferred versions thereof, other versions are possible. Therefore, the point and scope of the appended claims should not be limited to the description of the preferred versions contained herein.

As to a further discussion of the manner of usage and operation of the present invention, the same should be apparent from the above description. Accordingly, no further discussion relating to the manner of usage and operation will be provided. With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

That which is claimed is:

1. A device to clean a laparoscopic lens comprising: a laparoscopic lens cleaner is configured to be inserted into a body cavity, the laparoscopic lens cleaner comprising: a rigid rod; a flat, solid, one-piece, non-hollow stem without a housing, wherein the proximal end of the stem is attached to the center of the rod, and the stem is configured to extend perpendicularly away from the rod and includes multiple curves along the length thereof; a tip at the distal end of the stem, wherein the tip is flat, has the same width as the stem, and extends longitudinally along a common axis/line as the stem; wherein the tip cleans the laparoscopic lens while extended longitudinally along the common axis/line; and wherein the ends of the rod is are bent towards the tip.

2. The device according to claim 1, wherein the tip is made of a soft, absorbent material.

3. The device according to claim 1, wherein the device is made of plastic.

4. The device according to claim 3, wherein the device is disposable.

5. The device according to claim 1, wherein the tip is fixed in a longitudinally position along the common axis/line.

6. The device according to claim 1, wherein the tip is not meshed.

7. The device according to claim 1, wherein the laparoscopic lens does not need to be repositioned to be cleaned.

\* \* \* \* \*